United States Patent [19]

Fochtman et al.

[11] Patent Number: 4,697,457
[45] Date of Patent: Oct. 6, 1987

[54] WASTE MATERIAL COMPRESSION TESTER

[75] Inventors: Edward G. Fochtman, Elmhurst; Carl P. Swanstrom, Crestwood, both of Ill.

[73] Assignee: Chemical Waste Management, Inc., Oak Brook, Ill.

[21] Appl. No.: 835,678

[22] Filed: Mar. 3, 1986

[51] Int. Cl.⁴ .............................................. G01N 3/08
[52] U.S. Cl. .......................................... 73/820; 73/76
[58] Field of Search .................... 73/820, 76, 818, 825, 73/821, 823, 153, 73; 100/99

[56] References Cited

U.S. PATENT DOCUMENTS

| | | |
|---|---|---|
| 1,914,686 | 6/1933 | Eddington . |
| 2,082,364 | 6/1937 | Store . |
| 2,343,340 | 3/1944 | Stevens . |
| 3,282,115 | 11/1966 | Taylor et al. . |
| 3,979,947 | 9/1976 | Parkinson ............................ 73/73 |
| 4,095,459 | 6/1978 | Feldt .................................... 73/76 |
| 4,184,424 | 1/1980 | Yeager et al. ..................... 100/99 |

FOREIGN PATENT DOCUMENTS 370984  4/1932  United Kingdom .................. 73/73

Primary Examiner—Jerry W. Myracle
Attorney, Agent, or Firm—Sughrue, Mion, Zinn, Macpeak, and Seas

[57] ABSTRACT

A waste material compression tester is provided and having a reservoir or chamber for holding a sample of waste material containing liquid, a pressure source to apply pressure to the waste material under a pre-set pressure and a predetermined time period and a detector to indicate whether liquid was exuded from the waste material after the pressure is removed.

9 Claims, 5 Drawing Figures

4,697,457

WASTE MATERIAL COMPRESSION TESTER

BACKGROUND OF THE INVENTION

1. Field of the Invention

This invention pertains to an apparatus for testing a sample of waste material to determine the tendency of the sample to exude liquid. The invention may be used for wastes as received, or after sludges or liquid wastes have been stabilized.

2. Background of the Prior Art

The prior art show various devices for expressing liquid from material to determine the moisture content thereof.

SUMMARY OF THE INVENTION

Liquid or semi-liquid waste material stabilized with chemical reactants is disposed of in landfills. Due to the pressure exerted on the waste material by the weight in the landfills, some liquid may be expressed from the waste material with the result that the expressed liquid may damage the landfill or cause an environmental impact.

Therefore, there is a need for a simple yet effective test device to evaluate the tendency of a waste to exude liquid.

It is therefore an object of the invention to provide a device to test whether a sample of waste material will exude liquid when subject to pressures which may be experienced in a landfill which device includes a reservoir to hold a small sample of waste material to be tested.

It is yet another object of the invention to provide a reservoir for a sample of waste material and a pressure source to place the waste material under a pre-set pressure.

And yet another object of the invention is to provide a detector to indicate whether the waste material placed under pressure exuded liquid.

Still another object of the invention is to provide a container to capture exuded liquid from the sample of waste material.

These and other objects of the invention will become apparent to those skilled in the art to which the invention pertains from a reading of the specification when taken in light of the annexed drawings.

DESCRIPTION OF THE PREFERRED EMBODIMENT OF THE INVENTION

Figure 1:
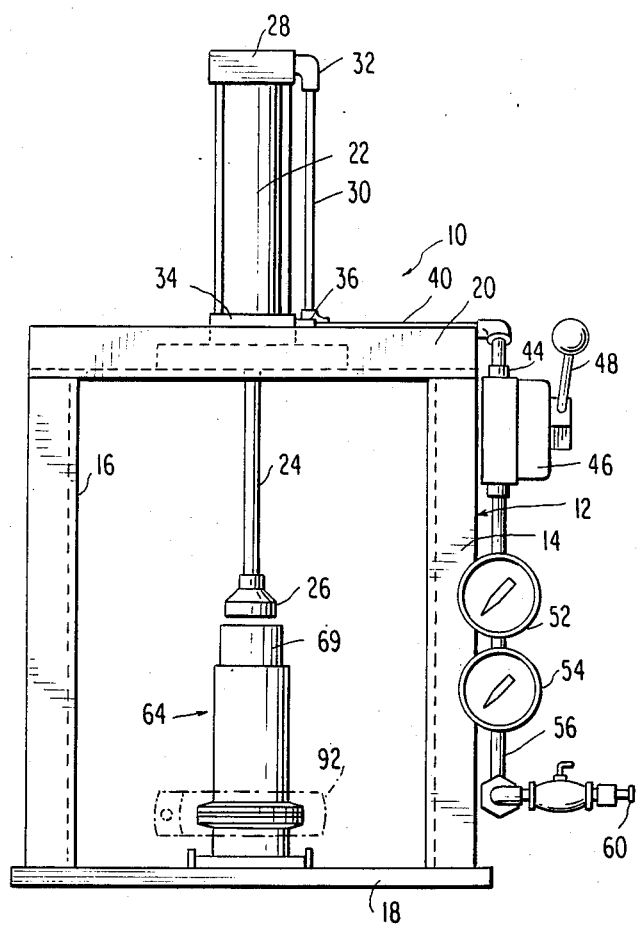
FIG. 1 is a perspective view of the waste material tester including the pressure source, waste material sample reservoir, liquid capturing container and support base.
Figure 2:
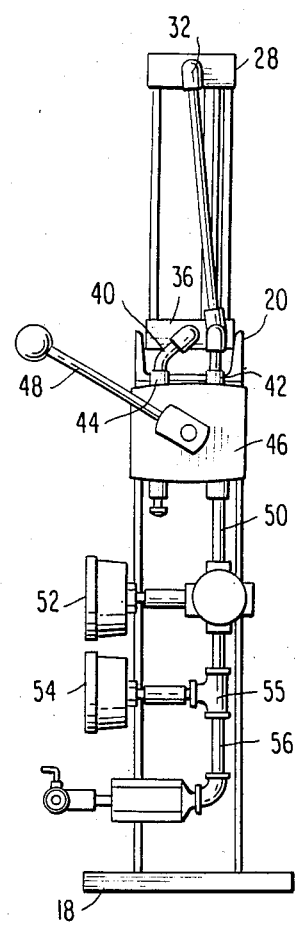
FIG. 2 is a side view of the device of FIG. 1 and shows pressure supplying conduits, meters and handle for activating a valve.
Figure 5:
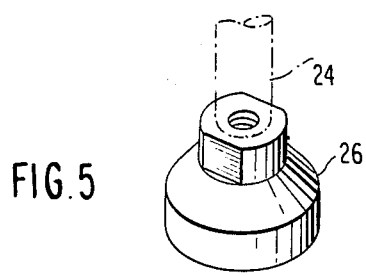
FIG. 5 is a view in section of the piston head.

Referring now in more detail to the drawings, FIG. 1 shows a pressure applying device 10 including a frame 12 having uprights 14 and 16, a base plate 18 secured to the lower ends of the uprights and a top 20 secured to the upper ends of the uprights. The top 20 supports a cylinder 22 and its associated piston 24 having a head 26. The cylinder 22 is capped at 28 and has a pressure conveying conduit 30 having one end 32 extending through the cap 28 to the interior of the cylinder 22. The base of the cylinder 22 has a cap 34 with an aperture through the center thereof to permit movement of the piston 24. There is an aperture extending axially through the cap 34 to receive one end 36 of a pressure conduit 40. Both ends 42 and 44 of the conduits enter a control valve 46 having a valve actuating handle 48. Extending from the valve 46 is a pressure supplying conduit 50 having pressure indicating gages 52 and 54 suitably affixed thereto by connections 55. A source of pressure (not known) is attached to the conduit 60 as is well known in the art.

Figure 3:
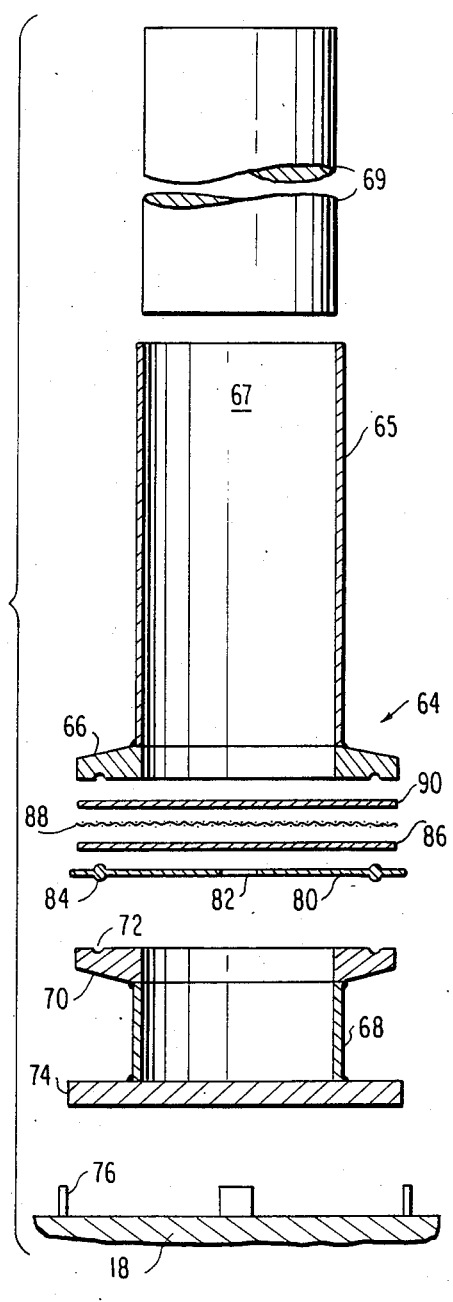
FIG. 3 is a perspective view in section of the waste material sample reservoir, liquid capturing container and liquid detector assembly.
Figure 4:
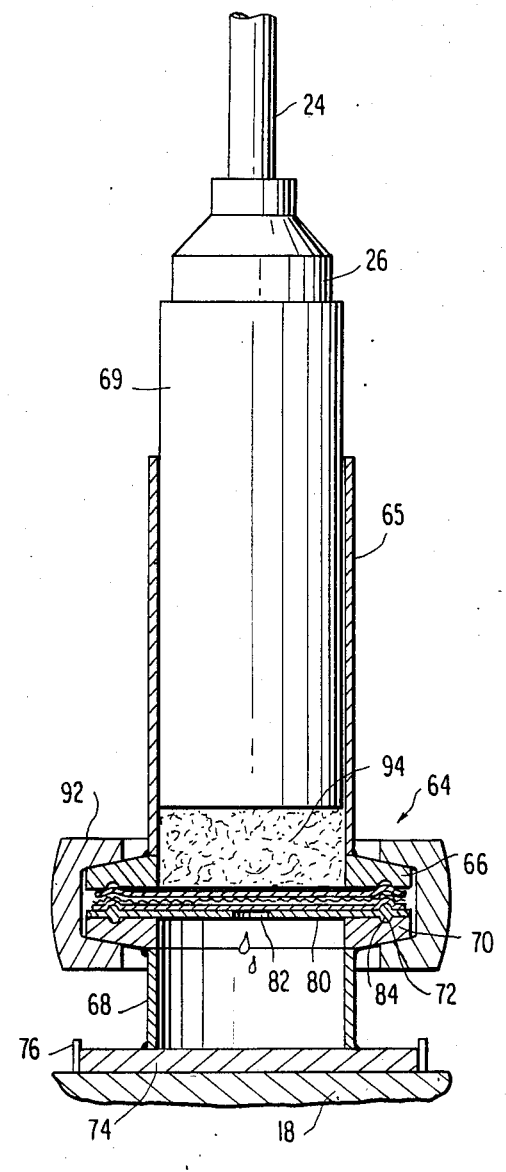
FIG. 4 is a perspective view in section of the reservoir for containing a sample of waste material, liquid detector, liquid capturing container, and pressure applying piston.

Supported for test on the base 18 is a waste material reservoir assembly 64 as best seen in FIGS. 3 and 4. The assembly 64 comprises a pipe section 65 defining a reservoir or chamber 67 for holding a sample of waste material and having a flange 66 below which there is a liquid capturing container 68 having a support flange 70 with a continuous ridge 72 thereabout. Cylindrical member 69 is slightly less in diameter than the diameter of section 65 which is used in conjunction with cylinder 24 to pressurize a waste material sample in chamber 67. The cylinder may be solid and is manually removable from the chamber 67. The lower end of the container 68 has a flange 74 which cooperates with alignment guide 76 on the base 18. Supported on the flange 70 is a support plate 80 having a center aperture 82 therethrough for the passage of liquid. The plate 80 is circular and has a continuous bead 84 which is supported in the continuous ridge 72 in the flange 70 of the container 68. A first or bottom filter material 86 rests on and covers the plate 80. A screen 88 rests on and covers the bottom filter 86 and a second or top filter 90 rests on and covers the screen 88.

FIG. 4 shows the assembled components and it will be appreciated that the ends or peripheries of the elements 80, 86, 88 and 90 are caught between the flanges 66 and 70 and are held together by clamp 92.

In operation, a sample 94 of waste material is inserted into the reservoir or chamber 67 and rests on the top filter material 90. The assembly 64 is placed on the base 18 with the flanges 74 in the alignment guides 76. The pressure actuating handle 48 is operated permitting pressure to enter the cylinder and thus force the piston 24 downwardly whereby the head 26 contacts the solid cylinder 69 which in turn contacts the sample 94. The head 26 is slightly less in diameter than the reservoir or chamber 67, and the solid cylinder 69 so that the sample 94 is substantially covered thereby. It will be understood that the pressure exerted on waste material in a landfill will be approximately known so that the pressure applied by the apparatus may be pre-set to that known pressure.

The waste material sample will have a given liquid to solid ratio and the pre-set pressure and time period will be selected to determine the tendency of the sample to exude liquid. Should liquid be exuded from the sample, it will contact the filter material 90 and discolor same. If sufficient liquid is exuded, it will pass on through the filter material 90, the screen 88 and contact the filter material 86 and discolor the same. Excess liquid so exuded will pass through the filter material 86 and pass through aperture 82 to be captured in container 68. After the predetermined time period has elapsed, the pressure is released and the piston raised in a manner well-known in the art. The assembly 64 is removed from the base 18 and the sample discarded. The clamp is removed and the filter papers are examined to determine whether liquid was exuded from the sample. A discoloration on the lower filter 86 would indicate that waste liquid was exuded in sufficient quantity thus indicating that the waste material from which the sample was taken is unsuitable for landfill and must be further treated.

While the invention has been explained with respect to a preferred embodiment thereof, it is contemplated that various changes may be made in the invention without departing from the spirit and scope thereof.

What is claimed is:

1. A waste material, compression tester comprising:
   a reservoir for holding a sample of waste material containing liquid;
   said reservoir has a waste material sample chamber, a waste liquid capturing container, and means between said chamber and container to detect the passage of exuded liquid;
   pressure means to apply pressure to the waste material; and
   a support for the reservoir.

2. A waste material, compression tester according to claim 1, wherein:
   said detecting means comprises first and second detecting means on a support plate having a central aperture for the passage of exuded liquid.

3. A waste material, compression tester according to claim 2; and:
   said support plate has a continuous bead co-acting with a recess in a flange of a liquid capturing container.

4. A waste material, compression tester according to claim 1, wherein:
   said support is a plate having alignment guides for said liquid capturing container.

5. A waste material, compression tester according to claim 1, and:
   said detecting means is a first filter material on which a waste sample is supported and a lower filter material supported on a support plate between which a screen is positioned.

6. A waste material, compression tester according to claim 5, and:
   said first filter is discolored by the passage of exuded and said lower filter is discolored by the passage of exuded liquid thus indicating the passage of exuded liquid, whereby when the second filter is discolored said discoloration is a determination that the waste material from which said sample was taken is unfit for disposal in a landfill.

7. A waste material, compression tester according to claim 4, and:
   said first detecting means is a filter medium positioned on the support plate and said second detecting means is a filter medium separated from the first filter medium by a screen.

8. A waste material compression tester comprising:
   a reservoir for holding a sample of waste material containing liquid;
   pressure means to apply pressure to the waste material;
   means in the reservoir for detecting the passage of exuded liquid;
   a support for the reservoir;
   means for capturing exuded liquid and;
   said means for capturing exuded liquid is a container having a top flange with a continuous recess therein and a bottom flange and said support having alignment guides for receiving said bottom flange.

9. A waste material, compression tester according to claim 8, and:
   said reservoir, detecting means and liquid capturing means in tandem and held together by clamp means.

* * * * *